United States Patent
Correia et al.

(10) Patent No.: US 9,676,735 B2
(45) Date of Patent: Jun. 13, 2017

(54) PROCESS FOR THE PREPARATION OF EFAVIRENZ AND DEVICES SUITABLE THEREFORE

(71) Applicant: MAX-PLANCK-GESELLSCHAFT ZUR FÖRDERUNG DER WISSENSCHAFTEN E.V., Munich (DE)

(72) Inventors: Camille A. Correia, Potsdam (DE); Kerry Gilmore, Brewster, MA (US); David Tyler McQuade, Tallahassee, FL (US); Peter H. Seeberger, Kleinmachnow (DE)

(73) Assignee: Max-Planck-Gesellschaft zur Förderung der Wissenschaften e.V., Munich (DE)

(*) Notice: Subject to any disclaimer, the term of this patent is extended or adjusted under 35 U.S.C. 154(b) by 0 days.

(21) Appl. No.: 14/837,500

(22) Filed: Aug. 27, 2015

(65) Prior Publication Data

US 2017/0057937 A1    Mar. 2, 2017

(51) Int. Cl.
| | |
|---|---|
| *C07D 265/18* | (2006.01) |
| *C07C 265/12* | (2006.01) |
| *B01J 19/00* | (2006.01) |
| *C07F 1/08* | (2006.01) |
| *C07C 29/00* | (2006.01) |
| *C07C 29/68* | (2006.01) |
| *C07C 45/00* | (2006.01) |
| *C07C 33/50* | (2006.01) |

(52) U.S. Cl.
CPC ........ *C07D 265/18* (2013.01); *B01J 19/0013* (2013.01); *C07C 29/00* (2013.01); *C07C 29/68* (2013.01); *C07C 33/50* (2013.01); *C07C 45/00* (2013.01); *C07C 265/12* (2013.01); *C07F 1/08* (2013.01); *B01J 2219/00051* (2013.01); *B01J 2219/00162* (2013.01); *C07C 2101/02* (2013.01)

(58) Field of Classification Search
CPC .................................................. C07D 265/18
See application file for complete search history.

(56) References Cited

U.S. PATENT DOCUMENTS

| | | |
|---|---|---|
| 2012/0114534 A1 | 5/2012 | Van Der Heijden |
| 2013/0330246 A1 | 12/2013 | Stemmet |

FOREIGN PATENT DOCUMENTS

| | | |
|---|---|---|
| WO | WO 96/37457 | 11/1996 |
| WO | WO 98/14436 | 4/1998 |
| WO | WO 98/05676 | 11/1998 |
| WO | WO 2012/079235 | 6/2012 |
| WO | WO 2012/097510 | 7/2012 |
| WO | WO 2012/975511 | 7/2012 |

OTHER PUBLICATIONS

Correia et al., "A Concise Flow Synthesis of Efavirenz" *Angew. Chem. Int. Ed.* (2015) 54:4945-4948.

Correia, et al., "Copper(I)/N-Heterocyclic Carbene (NHC)-Catalyzed Addition of Terminal Alkynes to Trifluoromethyl Ketones for Use in Continuous Reactors" Adv. Synth. Catal. (2013) 355:3517-3521.

Jiang, et al., "-(Trifluoromethyl)ethenyl boronic acid as a useful trifluoromethyl containing building block. Preparation and palladium-catalysed coupling with aryl halides" Tetrahedron Letters (2001) 42:4083-4085.

Thompson, et al., Use of an Ephedrine Alkoxide to Mediate Enantioselective Addition of an Acetylide to a Prochiral Ketone: Asymmetric Synthesis of the Reverse Transcriptase Inhibitor L-743,726. Tetrahedron Letters (1995) 36(49):8937-8940.

*Primary Examiner* — Kahsay Habte
(74) *Attorney, Agent, or Firm* — Knobbe, Martens, Olson & Bear, LLP (57) ABSTRACT

The invention relates to a process for the preparation of Efavirenz via an efficient transition metal catalyzed cyclization, to a device suitable to perform such process as well as to novel intermediates.

19 Claims, 3 Drawing Sheets

PROCESS FOR THE PREPARATION OF EFAVIRENZ AND DEVICES SUITABLE THEREFORE

The invention relates to a process for the preparation of Efavirenz via an efficient transition metal catalyzed cyclization, to a device suitable to perform such process as well as to novel intermediates.

BACKGROUND OF THE INVENTION

Efavirenz, (4S)-6-chloro-4-(2-cyclopropylethynyl)-4-(trifluoromethyl)-1H-3,1-benzoxazin-2-one, is one of the preferred agents used in combination therapy for first-line treatment of human immunodeficiency virus (HIV).

(Efavirenz)

The synthesis of efavirenz and structurally similar reverse transcriptase inhibitors are for example disclosed in WO 95/20389, the asymmetric synthesis of an enantiomeric benzoxazinone by an enantioselective acetylide addition and cyclization sequence is disclosed in Thompson, et al., Tetrahedron Letters 1995, 36, 8937-8940 and WO 96/37457.

WO 98/51676 A to Merck discloses the method for preparation of efavirenz starting from 4-chloro aniline. Due to the nature of the amino group, this method however requires protection and deprotection steps making the overall process cumbersome.

In Jiang, Wang and Yang in Tett. Lett (2001), 42 (24), 4083-4085 a process is disclosed which avoids such protection and deprotection steps by application of a five step procedure starting from nitro-bromo-chlorobenzene. This method requires reactions including the use of sodium iodate and osmium tetroxide, a palladium catalyzed coupling reaction and a nickel catalyzed reduction to obtain trifluoromethyl-(2-amino-5-chloro-phenyl)ketone. Subsequent steps to the final product efavirenz include the ring closure of (S)-2-(2-amino-5-chlorophenyl)-4-cyclopropyl-1,1,1-trifluorobut-3-yn-2-ol using phosgene or derivatives thereof.

The high toxicity and limited availability of at least some the required reagents, however, exclude this process from being applied on industrial scale.

WO2012079235, WO201297510 and WO201297511 to Lonza disclose a short route to efavirenz starting from 1,4-dichlorobenzene. However, cyclization of the intermediate (4S)-4-cyclopropyl-2-(2,5-dichloro-phenyl)-1,1,1-trifluoro-but-3-yn-2-ol is effected by first converting the hydroxy moiety into a carbamate using chlorosulphonylisocyanate and subsequent ring closure applying a copper catalyzed Ullmann-type reaction. The overall yield however were only up to 45% and thus too low to allow commercial application.

Therefore, there was still a need for a short and efficient route to efavirenz using readily available reagents.

DESCRIPTION OF THE INVENTION

There is now provided a process for the preparation of 6-chloro-4-(2-cyclopropylethynyl)-4-(trifluoromethyl)-1H-3,1-benzoxazin-2-one comprising at least the step of reacting 4-cyclopropyl-2-(2,5-dichloro-phenyl)-1,1,1-trifluoro-but-3-yn-2-ol with at least one cyanate in the presence of at least one transition metal compound.

As used herein the term cyanate denotes the chemical compound formally comprising one or more cyanate anions (N=C=O$^-$) and one or more cations, in particular metal cations.

One skilled in the art, however, is aware that, depending of the nature of the cation the type of bonding of the cyanate to the metal may be from mainly ionic, like for alkali metals to more covalent or coordinative e.g. for transition metals.

Suitable cyanates include alkali cyanates such as lithium, sodium and potassium cyanate, alkaline earth cyanates such as calcium cyanate and transition metal cyanates.

A preferred cyanate is sodium cyanate.

The amount of cyanate used is for example in a range of from 0.8 to 50 mol of cyanate per mol of 4-cyclopropyl-2-(2,5-dichloro-phenyl)-1,1,1-trifluoro-but-3-yn-2-ol employed, preferably of from 1 to 40 mol, more preferably of from 2 to 40 mol, for example 2, 20 or 40 mol, whereby the aforementioned molar ratios are calculated on the moles of cyanate anions present in the cyanates.

Examples of suitable transition metal compounds include copper, nickel, palladium, rhodium and platinum compounds.

In one embodiment the transition metal compounds are selected from those of formulae (Ia) and (Ib)

$$M(Y^1)_2 \quad (Ia),$$

$$M(Y^2) \quad (Ib),$$

wherein
M is nickel, palladium or copper(II) and
$Y^1$ is chloride, bromide, acetate, nitrate, methanesulphonate, trifluoromethanesulphonate, trifluoroacetate or acetylacetonate
$Y^2$ is sulphate
or those of formulae (IIa) and (IIb)

$$MY^3 \quad (IIa)$$

$$[M(B)_4](Y^3) \quad (IIb)$$

wherein
M is copper (I) and
$Y^3$ is chloride, bromide, iodide, acetate, methanesulphonate, trifluoromethanesulphonate, tetrafluoroborate, trifluoroacetate hexafluorophosphate, perchlorate, hexafluoroantimonate, tetra(3,5-bistrifluoromethylphenyl)borate or tetraphenylborate and
B is a nitrile such as acetonitrile, benzonitrile or benzyl nitrile, or
or those of formula (III)

$$[M(D)_2] \quad (III)$$

wherein
M is palladium or nickel and
and
D is a ($C_4$-$C_{12}$)-diene such as norbornadiene or 1,5-cyclooctadiene, Formulae (Ia) and (Ib) also encompass the transition metal compounds in their hydrated form, such as for example copper(II) nitrate trihydrate and copper (II) sulphate pentahydrate etc.

Preference is given to using the following transition metal compounds:

copper (I)iodide, copper(II) triflate, copper (II) nitrate trihydrate, copper sulphate for example as pentahydrate or in dehydrated form, copper(I) tetraacetonitrile tetrafluoroborate.

In one embodiment the above mentioned transition metal compounds are used in combination with ligands capable of coordinating to copper, nickel or palladium, preferably copper ions.

Preferably those ligands are selected from the group consisting of diamines, carbenes, phosphines, phosphites phenanthrolines, hydroxyquinolines, bis imines, bipyridines, salicylamides, pyrrolidines, glycine, proline, sparteine, and mixtures thereof.

Specific Examples include phenanthroline, N,N'-dimethyl-1,2-diaminoethan (DMEDA) and N,N'-dimethyl-1,2-diaminocyclohexane (CyDMEDA).

Such ligands, in particular phenanthroline, N,N'-dimethyl-1,2-diaminoethan (DMEDA) and N,N'-dimethyl-1,2-diaminocyclohexane (CyDMEDA) are typically employed in an amount of from 0.5 to 10 mol per mol of copper, nickel or palladium compound employed and calculated on the copper, nickel or palladium content present in such compounds, preferably of from 1 to 5 mol and even more preferably of from 2 to 4 mol.

Specific combinations of transition metal compounds and ligands include combinations of copper (I)iodide with 2 or 4 mol of phenanthroline or DMEDA or CyDMEDA, copper (II) triflate benzene complex with 2 or 4 mol of phenanthroline or DMEDA or CyDMEDA, copper (II) nitrate trihydrate with 2 or 4 mol of phenanthroline or DMEDA or CyDMEDA, copper sulphate with 2 or 4 mol of phenanthroline or DMEDA or CyDMEDA, copper(I) tetraacetonitrile tetrafluoroborate with 2 or 4 mol of phenanthroline or DMEDA or CyDMEDA.

The aforementioned combinations with CyDMEDA and DMEDA are preferred.

In one embodiment the reaction is carried out in absence of phase transfer catalysts such as tetrabutylammonium chloride.

It is known to those skilled in the art that during their employment in the process according to the invention complexes are formed which are not encompassed by the aforementioned formulae (Ia), (Ib), (IIa), (IIb) and (III) and that such complexes may be pre-formed and also directly be used or applied as isolated transition metal compound.

Therefor the term transition metal compound also includes transition metal compounds e.g. obtained by reacting transition metal compounds of formulae (Ia), (Ib), (IIa), (IIb) and (III) with the ligands mentioned above.

In one embodiment, in particular where copper (II) compounds are employed it is possible to additionally use copper (0) e.g. in form of finely divided elemental copper i.e. copper powder. Preferably such copper powder is used with a particle size of below 200 micrometer, more preferably below 100 micrometer.

The amount of copper (0) employed per mole of copper (II) compound is preferably of from 0.25 to 2 mol of copper (0) per copper (II) compound, preferably of from 0.4 to 1.2 mol, for example 0.5 mol or 1 mol, whereby the molar ratio is calculated on the amount of copper atoms present in the copper (II) compound.

The amount of transition metal compound used is for example in a range of from 0.0001 to 1.2 mol of transition metal compound per mol of 4-cyclopropyl-2-(2,5-dichlorophenyl)-1,1,1-trifluoro-but-3-yn-2-ol employed, preferably of from 0.01 to 1.0 mol, more preferably of from 0.08 to 0.5 mol, particularly preferably of from 0.1 to 0.2 mol, for example 0.1 or 0.2 mol, whereby the aforementioned molar ratios are calculated on the content of transition metal atoms within the transition metal compound.

Reaction times are generally in a range of from 20 min to 48 hours, preferably in a range of from 45 mins to 24 hrs. Longer reaction times are possible but typically have no positive effect. Where the reaction is carried out continuously, in particular in a flow reactor, reaction times are typically and surprisingly much shorter than in batch reactions. Conversion of the 4-cyclopropyl-2-(2,5-dichloro-phenyl)-1,1,1-trifluoro-but-3-yn-2-ol typically exceeds 90% already after 30 minutes.

The process according to the invention is typically carried out using an organic diluent. Examples of organic diluents include aromatic hydrocarbons such as benzene, toluene and xylenes, nitriles such as benzonitrile and acetonitrile, ethers or mixtures thereof, in particular toluene or mixtures of benzonitrile, acetonitrile and toluene.

The reaction temperature is typically of from 60 to 200° C., preferably 80 to 150° C. and more preferably of from 100 to 140° C., for example around 120° C. or around 130° C.

The reaction pressure is typically of from 0.05 MPa to 5 MPa, preferably of from 0.09 MPa to 1 MPa, for example 0.7 MPa.

The process may be carried out batchwise or continuously. A continuous process is preferably carried out in a flow-through reactor, in particular in a micro-fluidic device.

The process according to the invention typically produces 2-(3-chlorophenyl)-4-cyclopropyl-1,1,1-trifluoro-but-3-yn-2-ol as a byproduct in various amounts. Therefore the invention also encompasses both enantiomers of 2-(3-chlorophenyl)-4-cyclopropyl-1,1,1-trifluoro-but-3-yn-2-ol either in pure form or in any combination as well as mixtures comprising 6-chloro-2-cyclopropylethynyl-4-trifluoromethyl-1H-3,1-benz-oxazin-2-one and 2-(3-chlorophenyl)-4-cyclopropyl-1,1,1-trifluoro-but-3-yn-2-ol.

In one embodiment the molar ratio of 6-chloro-4-(2-cyclopropylethynyl)-4-(trifluoromethyl)-1H-3,1-benzoxazin-2-one and 2-(3-chlorophenyl)-4-cyclopropyl-1,1,1-trifluoro-but-3-yn-2-ol in such mixture is of from 1:1 to 1000:1, in another embodiment of from 2:1 to 10:1.

The invention further encompasses 4-cyclopropyl-2-(2-isocyanato-5-chloro-phenyl)-1,1,1-trifluoro-but-3-yn-2-ol and transition metal complexes, in particular, nickel, copper or palladium, more particularly copper complexes containing 4-cyclopropyl-2-(2-isocyanato-5-chloro-phenyl)-1,1,1-trifluoro-but-3-yn-2-ol. The afore-mentioned compounds are formed as intermediates during the process according to the invention.

The desired 6-chloro-4-(2-cyclopropylethynyl)-4-(trifluoromethyl)-1H-3,1-benzoxazin-2-one produced according to the invention may be isolated and further purified by procedures well known to those in the art.

In one embodiment 6-chloro-4-(2-cyclopropylethynyl)-4-(trifluoromethyl)-1H-3,1-benzoxazin-2-one is obtained after solvent removal and recrystallization and/or precipitation.

Recrystallization may be effected using hexane dichloromethane mixtures or isopropanol. Precipitation may be effected using isopropanol and precipitating the purified 6-chloro-4-(2-cyclopropylethynyl)-4-(trifluoromethyl)-1H-

3,1-benzoxazin-2-one using water isopropanol mixtures, e.g. in a ration of 30/70 by volume.

If not explicitly mentioned otherwise, the terms 6-chloro-4-(2-cyclopropylethynyl)-4-(trifluoromethyl)-1H-3,1-benzoxazin-2-one, 4-cyclopropyl-2-(2,5-dichloro-phenyl)-1,1,1-trifluoro-but-3-yn-2-ol, 2-(3-chlorophenyl)-4-cyclopropyl-1,1,1-trifluoro-but-3-yn-2-ol and 4-cyclopropyl-2-(2-isocyanato-5-chloro-phenyl)-1,1,1-trifluoro-but-3-yn-2-ol denote and encompass their pure (4S) or (4R) enantiomers or any mixture thereof, in particular the racemate.

In a preferred embodiment, since efavirenz has 4S configuration, 4-cyclopropyl-2-(2,5-dichloro-phenyl)-1,1,1-trifluoro-but-3-yn-2-ol is employed with an enantiomeric excess (ee) of at least 80%, preferably at least 90% and even more preferably at least 95%.

Since no effect on the stereocenter is to be expected is typically obtained with the same stereoconfiguration as the starting material.

Thus, (4S)-4-cyclopropyl-2-(2,5-dichloro-phenyl)-1,1,1-trifluoro-but-3-yn-2-ol thus leads to (4S)-4-cyclopropyl-2-(2-isocyanato-5-chloro-phenyl)-1,1,1-trifluoro-but-3-yn-2-ol and finally to efavirenz, (4S)-6-chloro-4-(2-cyclopropylethynyl)-4-(trifluoromethyl)-1H-3,1-benzoxazin-2-one.

Devices Suitable to Perform the Invention

The process can be carried out using any type of reactor suitable therefor. This includes batch reactors such as stirred tank reactors as well as flow-through reactors, in particular microfluidic devices.

Preferably, the process according to the invention is carried out in a flow-through reactor. Examples of suitable flow-through reactors include the flow-through reactors, in particular microfluidic devices disclosed in US2013/330246 and US2012/114534.

In a preferred embodiment, which is also encompassed by this invention the flow-through reactor in particular the micro-fluidic device comprises at least
  a feeding zone comprising a pump
  a reaction zone which is connected to means to control temperature in said first reaction zone, in particular at levels of 80 to 200° C. such as a heater and further comprises
    a cyanate and
    preferably additionally copper powder and/or, preferably and
      an inorganic material selected from the group consisting of aluminium and or silicon compounds such as celite or alumina, preferably celite.
  an outlet zone
whereby the flow-through reactor in particular the microfluidic device further comprises a pressure control device.

The feeding zone may additionally be equipped with standard mixing elements such as static mixing elements, stirrers, micromixers and the like.

Figure 1:
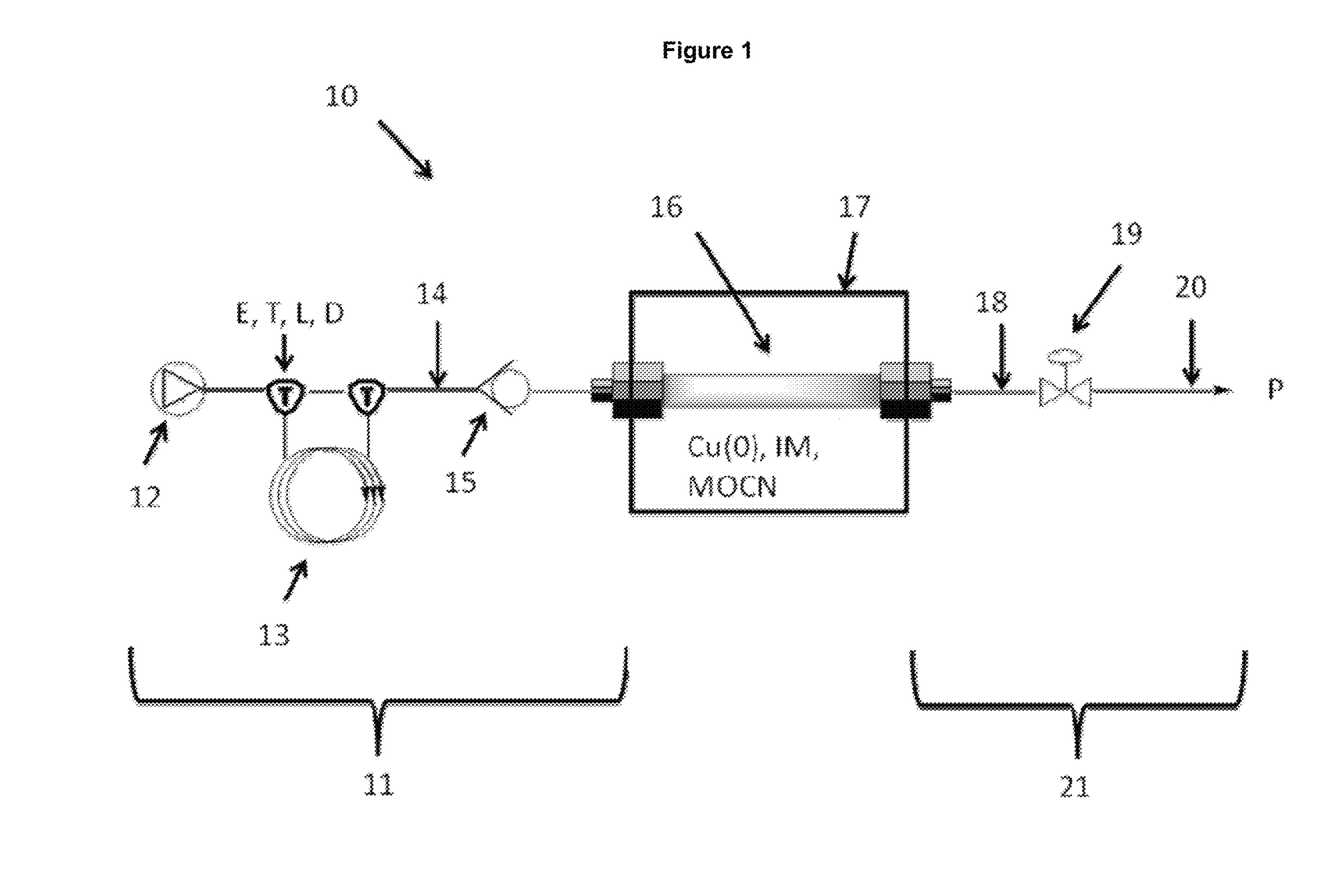
FIG. 1 shows an exemplary, simplified flow diagram of a process according to the invention using a flow-through reactor 10.

FIG. 1 further illustrates the device according to the invention.

FIG. 1 is an exemplary, simplified flow diagram of a process according to the invention using a flow-through reactor 10.

The feeding zone 11 comprises an injection loop 12 for feeding 4-cyclopropyl-2-(2,5-dichloro-phenyl)-1,1,1-trifluoro-but-3-yn-2-ol (E), transition metal compound (M), ligand (L) and organic diluent (D). The pump 13 conveys the reaction mixture via line 14 and check valve 15 to the reaction zone 16 comprising copper powder (Cu(0)), Celite as inorganic material (IM) and sodium cyanate (MOCN) which is heated by a heater 17. After leaving the reaction zone 16 the resulting product mixture P conveyed to the outlet zone 21 comprising exit line 18, pressure regulation device 19 and product exit line 20 to collection for further workup or storage.

In one embodiment the starting material 4-cyclopropyl-2-(2,5-dichloro-phenyl)-1,1,1-trifluoro-but-3-yn-2-ol is obtained by a process comprising at least the steps of A) metalating 1,4-dichlorobenzene of formula (IV) to obtain a metalated compound of formula (V) wherein M is a metal preferably lithium or potassium and (IV)

(V)

B) and reacting the metalated compound of formula (V) with trifluoroacetic acid anhydride, trifluoroacetyl halides such as trifluoroacetyl chloride or trifluoroacetic acid esters or trifluoroacetic acid amides such as trifluoroacetyl morpholine or mixtures thereof to obtain 1-(2,5-dichlorophenyl)-2,2,2-trifluoroethanone of formula (VI) and (VI)

C) reacting 1-(2,5-dichlorophenyl)-2,2,2-trifluoroethanone with a compound of formula (VII) to obtain a compound of formula (VIII) and (VII)

(VIII)

D) protonating the compound of formula (VIII) to obtain 4-cyclopropyl-2-(2,5-dichloro-phenyl)-1,1,1-trifluoro-but-3-yn-2-ol.

The reaction sequence comprising steps A), B), C) and D) including step C) with asymmetric induction is in principle known from WO2012079235, WO201297510 and WO201297511 which are herein incorporated by reference.

In step A) 1,4-dichlorobenzene of formula (IV) is metalate to obtain a metalated compound of formula (V).

Metallation is effected using a base which is preferably selected from the group consisting of n-butyl lithium, sec-butyl lithium, tert-butyl lithium, phenyl lithium and methyl lithium whereby n-butyl lithium is preferred. To assist deprotonation chelating compounds such as N,N,N',N'-tetraethylenediamine (TMEDA) may employed along with the base. In the aforementioned cases M stands for lithium. The aformentioned lithium bases may be employed in combination with potassium tert-butoxide to form so called Schlosser bases. In these cases M may stand for lithium or potassium.

The amount of base employed in step A) is typically from 0.7 to 2.5 mol per mol of 1,4-dichlorobenzene, preferably from 0.8 to 1.5 mol and more preferably from 0.8 to 1.1 mol.

The concentration of the base employed in step A) is typically from 0.5 to 3.3 mol per liter, in particular where step A) is performed using a flow-through reactor.

The concentration of 1,4-dichlorobenzene in a organic diluent employed in step A) is typically from 0.5 to 2.5 mol per liter, in particular where step A) is performed using a flow-through reactor.

In step A), the reaction temperature is for example of from −90 to 20° C., more preferably of from −60 to −20° C., even more preferably of from −60 to −30° C.

In one embodiment, the reaction pressure in step A) is from ambient pressure to 2 MPa, more preferably of from 0.2 to 1 MPa.

In one embodiment, the reaction time in step A) is from 1 min to 2 h, more preferably from 3 to 30 minutes.

In one embodiment, step A) is performed in an organic diluent which are preferably selected from the group consisting of aromatic and aliphatic hydrocarbons such as benzene, toluene, xylene, mesitylene, hexane and cyclohexane, ethers such as tert.butyl methyl ether, dioxane, tetrahydrofurane, methyltetrahydrofurane, dialkylethers of ethyleneglycol or polyethyleneglycols such as dimethoxyethane or diethoxyethane or mixtures of the aforementioned hydrocarbons and ethers.

The same applies to step B), since the compounds of formula (V) are typically not isolated.

In step B) the compounds of formula (V) are reacted with trifluoroacetic acid anhydride, trifluoroacetyl halides such as trifluoroacetyl chloride or trifluoroacetic acid esters or trifluoroacetic acid amides such as trifluoroacetyl morpholide or mixtures thereof.

The amount of trifluoroacetic acid anhydride, trifluoroacetyl halides such as trifluoroacetyl chloride or trifluoroacetic acid esters or trifluoroacetic acid amides such as trifluoroacetyl morpholide employed in step B) is typically from 0.7 to 1.5 mol per mol of 1,4-dichlorobenzene originally employed in step A), preferably from 0.8 to 1.5 mol and more preferably from 0.8 to 1.1 mol.

Trifluoroacetic acid anhydride, trifluoroacetyl halides such as trifluoroacetyl chloride or trifluoroacetic acid esters or trifluoroacetic acid amides such as trifluoroacetyl morpholide are typically employed in step B) as a solution in an organic diluent as disclosed above, preferably in the same solvent employed in step A). The concentration of trifluoroacetic acid anhydride, trifluoroacetyl halides such as trifluoroacetyl chloride or trifluoroacetic acid esters or trifluoroacetic acid amides in such solutions is typically from 0.2 to 2.5 mol per liter, in particular where step A) is performed using a flow-through reactor.

To obtain 1-(2,5-dichlorophenyl)-2,2,2-trifluoroethanone step B) may, depending on the trifluoroacetyl reagent employed, optionally be followed by quenching the reaction with a proton source.

Suitable proton sources include water, alcohols, phenols, carboxylic acids, mineral acids such as hydrochloric acid, sulfuric acid, ammonium salts and the like.

In step C) 1-(2,5-dichlorophenyl)-2,2,2-trifluoroethanone with a compound of formula (VII) to obtain a compound of formula (VIII).

In formula (VII) M denotes a metal or a metal complex fragment, preferably selected from the group consisting of Li, K, Na, MgHal with Hal being Chloride, Bromide or Iodide, one half equivalent of Mg or Zn, Zn(Alkyl) such as Zn(methyl) or Zn(ethyl). Preferably M is Li.

Where M=Li the bases mentioned above for step A) may be employed to react cyclopropylacetylene with such bases to form compounds of formula (VII). Alternatively, Lithium-, sodium or potassium hydride may be employed. Other compounds of formula (VII) may be obtained by reacting compounds of formula (VII) where M is Li, K or Na with magnesium chloride, magnesium bromide, magnesium iodide, dimethyl zinc or diethyl zinc depending on the desired reactivity.

Where asymmetric induction is desired compounds of formula (VII) may be employed together with one or more chiral additives which are exhaustively listed e.g. in WO2012079235, WO201297510, WO98/51676 and WO201297511 and are herein incorporated by reference.

Such chiral additives include (1R,2S)-N-pyrrolidinyl-norephedrine, N-methylephedrine, ephedrine, N,N-dibenzylnorephedrine and chinchonine.

The amount of compound (VII) employed in step C) is typically from 0.7 to 1.5 mol per mol of 1-(2,5-dichlorophenyl)-2,2,2-trifluoroethanone of formula (VI), preferably from 0.8 to 1.5 mol.

The concentration of compound (VII) employed in step C) is typically from 0.5 to 3.3 mol per liter, in particular where step C) is performed using a flow-through reactor.

In step C), the reaction temperature is for example of from −90 to 20° C., more preferably of from −50 to −0° C., even more preferably of from −40 to −10° C.

In one embodiment, the reaction pressure in step A) is from ambient pressure to 2 MPa, more preferably of from 0.2 to 1 MPa.

In one embodiment, the reaction time in step C) is from 1 min to 2 h, more preferably from 3 to 40 minutes.

In one embodiment, step C) is performed in an organic diluent which are preferably selected from the group consisting of aromatic and aliphatic hydrocarbons such as benzene, toluene, xylene, mesitylene, hexane and cyclohexane, ethers such as tert.-butyl methyl ether, dioxane, tetrahydrofurane, methyltetrahydrofurane, alkanes and dilalkylethers of ethyleneglycol or polyethyleneglycols such as dimethoxyethane or diethoxyethane or mixtures of the aforementioned hydrocarbons and ethers.

More preferably, step C) is performed such that solutions comprising 1-(2,5-dichlorophenyl)-2,2,2-trifluoroethanone of formula (VI) resulting from step B) are employed without intermediate isolation.

Performance of step C) leads to compounds of formula (VIII) wherein M has the same meaning as for compounds of formula (VII). In order to obtain 4-cyclopropyl-2-(2,5-dichloro-phenyl)-1,1,1-trifluoro-but-3-yn-2-ol compounds of formula (VIII) are protonated in step D).

Protonation is for example effected using a suitable proton source. Suitable proton sources include water, alcohols, phenols, carboxylic acids, mineral acids such as hydrochloric acid, sulfuric acid, ammonium salts and the like.

Preferably, steps A), B), C) are performed under an inert atmosphere.

As mentioned above the reaction sequence comprising steps A), B), C) and D) including step C) with asymmetric induction is in principle known.

However, it was found that surprisingly, much higher yields can be obtained using flow chemistry.

Therefore, the invention further encompasses a process for the preparation of 4-cyclopropyl-2-(2,5-dichloro-phenyl)-1,1,1-trifluoro-but-3-yn-2-ol or the compounds of formula (VII) wherein either steps A) and B) or step C) are performed continuously. In one embodiment steps A) and B) and step C) are performed continuously.

Where steps A) and B) and C) are performed continuously it is preferred not to isolate the intermediate of formula (VI).

In one embodiment the continuous process steps are performed in a modular flow-through reactor, preferably in a modular micro-fluidic device.

In a preferred embodiment, which is also encompassed by this invention the flow-through reactor in particular the micro-fluidic device comprises at least a first feeding zone comprising at least two feed lines each equipped with a pump and connected to a first reaction zone which is connected to means to control temperature in said first reaction zone, in particular at levels of −90° to 50° C. preferably at levels of −50° C. to −5° C. e.g. by means of a chiller and which is further connected to a second feeding zone comprising at least one feed line equipped with a pump which is connected to a second reaction zone which is connected to means to control temperature in said second reaction zone jointly with or independently of the first reaction zone, in particular at levels of −90° to 50° C., preferably at levels of −50° C. to −5° C. e.g. by means of a chiller and which is optionally and preferably connected to a further reaction zone connected to the second reaction zone and which is connected to means to control temperature in said further reaction zone independently of the second reaction zone, in particular at levels of −50° to 50° C.

Each feeding zone may independently additionally be equipped with standard mixing elements such as static mixing elements, stirrers, micro-mixers and the like.

In one embodiment the ratio of the reaction volumes of the first and the second reaction zone is of from 1:1 to 1:10, preferably of from 1:2 to 1:8 and more preferably of from 1:3 to 1:8, for example 1:5 or 1:3 or 1:7.

Where a further reaction zone is present, in one embodiment the ratio of the reaction volumes of the second and the third reaction zone is of from 2 to 1 to 100:1, preferably of from 5:1 to 20:1, for example 10:1.

The aforementioned flow-through reactor in particular the micro-fluidic device is particularly useful to perform steps A) and B) described above.

In another but preferred embodiment, which is also encompassed by this invention the flow-through reactor in particular the micro-fluidic device further comprises at least a third feeding zone comprising at least two feed lines each equipped with a pump and connected to a third reaction zone which is connected to means to control temperature in said first reaction zone, in particular at levels of −90° to 50° C. preferably at levels of −50° C. to −5° C. e.g. by means of a chiller, whereby the third reaction zone is connected to a fourth feeding zone comprising at least one feed line optionally equipped with a pump and which is upstream connected to the second reaction zone or, where present, the further reaction zone and which is downstream connected to a fourth reaction zone which is connected to means to control temperature in said fourth reaction zone jointly with or independently of the third reaction zone, in particular at levels of −50° to 0° C., preferably at levels of −30° C. to 0° C. e.g. by means of a chiller and optionally and preferably a quenching zone connected to the fourth reaction zone.

Each feeding zone may independently additionally be equipped with standard mixing elements such as static mixing elements, stirrers, micro-mixers and the like.

In one embodiment the ratio of the reaction volumes of the third and the fourth reaction zone is of from 1:1 to 1:10, preferably of from 1:1 to 1:5 and more preferably of from 1:2 to 1:4, for example 1:3.

The aforementioned additional components of the flow-through reactor in particular the micro-fluidic device are particularly useful to perform steps C) and D) described above.

Figure 2:
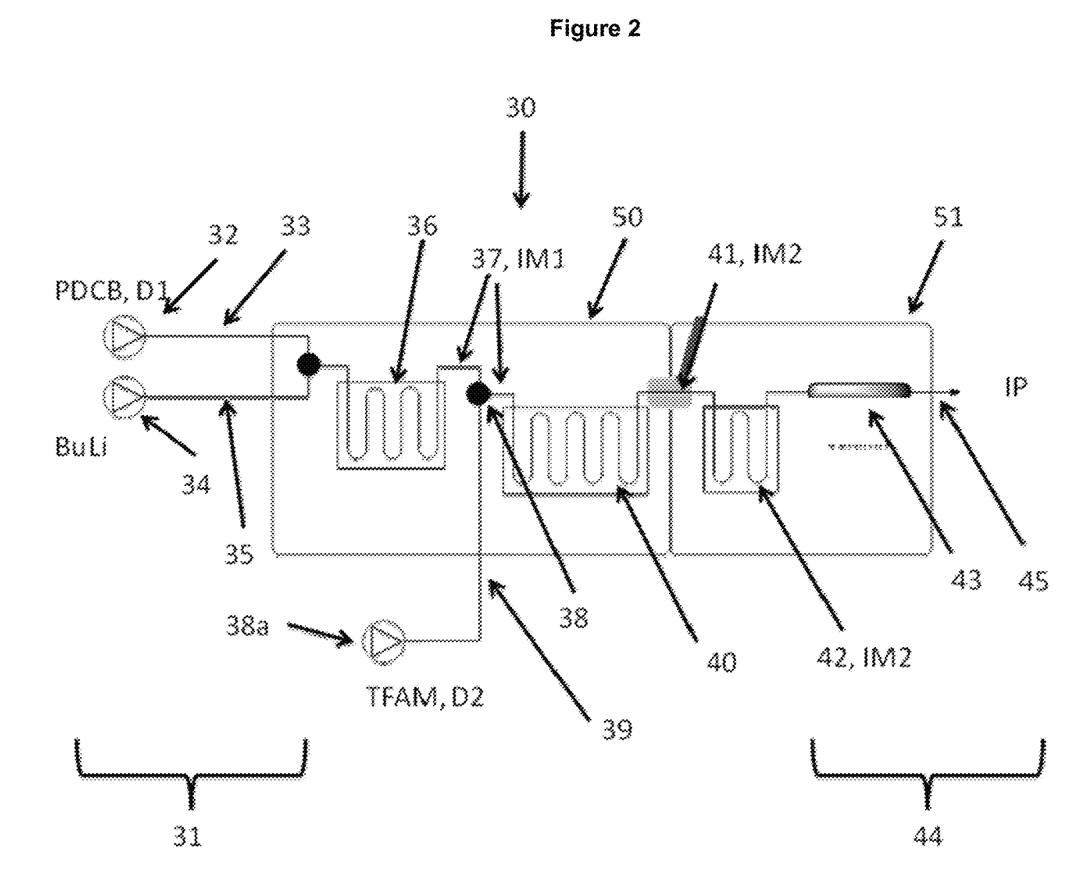
FIG. 2 shows an exemplary, simplified flow diagram of steps A) and B) in the process according to the invention using a flow-through reactor 30 having three reaction zones.
Figure 3:
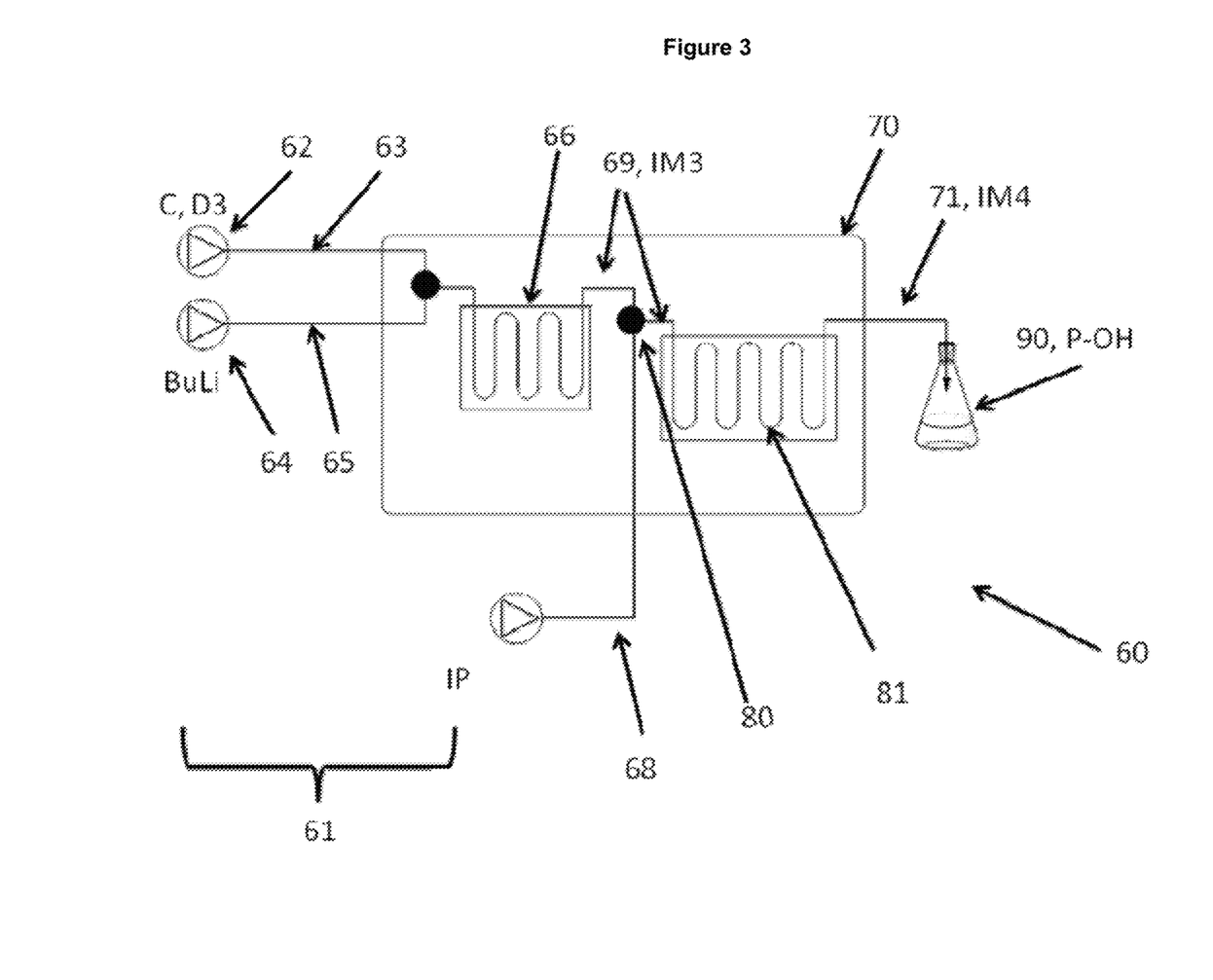
FIG. 3 shows an exemplary, simplified flow diagram of steps C) and D) in the process according to the invention using a flow-through reactor 60 having two reaction zones and a quenching zone.

FIGS. 2 and 3 further illustrate the device according to the invention.

FIG. 2 is an exemplary, simplified flow diagram of steps A) and B) in the process according to the invention using a flow-through reactor 30 having three reaction zones.

The first feeding zone 31 comprises a pump 32 for feeding 1,4-dichlorobenzene (PDCB) dissolved in an organic diluent (D1), such as THF via feed line 33 and a pump 34 for feeding n-butyllithium in hexanes (BuLi) via feed line 35 into the first reaction zone 36, which is cooled e.g. to −45° C. by a chiller 50, such as an ethanol cooling bath. After leaving the first reaction zone 36 the resulting Intermediate 1 of formula (V) (IM 1) is conveyed via line 37 to the second feeding zone 38 at which trifluoroacetyl morpholide (TFAM) dissolved in an organic diluent D2, which may be different or equal to D1, is fed by pump 38a via feed line 39 into line 37. Line 37 is connected to the second reaction zone 40, which is also cooled by a chiller 50 e.g. to −45° C. In the second reaction zone Intermediate 2 (IM2) is formed The second reaction zone 40 is connected via line 41 to a further reaction zone 42 which is independently cooled by a chiller 51 e.g. to a temperature of −10° C. The further reaction zone 42 is, via scavenging column 43, connected to the outlet zone 44 where 1-(2,5-dichlorophenyl)-2,2,2-trifluoroethanone of formula (VI) as intermediate product (IP) may exit the reactor via line 45 for further workup or storage or in one embodiment enter the fourth feeding zone 80 as described below.

The scavenging column 43 is for example filled with silica and serves to remove morpholine released in step B).

FIG. 3 is an exemplary, simplified flow diagram of steps C) and D) in the process according to the invention using a flow-through reactor 60 having two reaction zones and a quenching zone.

The third feeding zone 61 comprises a pump 62 for feeding cyclopropylacetylene (C) dissolved in an organic diluent (D3), such as THF via feed line 63 and a pump 64 for feeding n-butyllithium in hexanes (BuLi) via feed line 65 into the third reaction zone 66, which is cooled e.g. to −20° C. by a chiller 70, such as an ethanol cooling bath. After leaving the third reaction zone 66 the resulting Intermediate 3 of formula (VII) (IM 3) is conveyed via line 67 to the fourth feeding zone 80 at which the solution of 1-(2,5-dichlorophenyl)-2,2,2-trifluoroethanone of formula (VI) as intermediate product (IP) obtained as described above is fed via feed line 68 into line 69. Line 69 is connected to the fourth reaction zone 81, which is also cooled by the chiller 70 e.g. to −20° C. In the fourth reaction zone Intermediate 4 (IM4) is formed. The fourth reaction zone 81 is connected via line 71 to a quenching zone where 4-cyclopropyl-2-(2-isocyanato-5-chloro-phenyl)-1,1,1-trifluoro-but-3-yn-2-ol is obtained by protonation of the intermediate IM4 as product (P—OH) and exits the reactor e.g. for further workup.

The general components are well known to those skilled in art and may be constructed from any material that is fit for the intended purpose disclosed above.

The process according to the invention as well as the process to perform steps A) and B) and preferably also steps C) and D) using the flow-through reactors according to the invention allow the overall synthesis of efavirenz or its intermediates in unprecedented yield and efficiency.

The following examples further describe the invention in details without limiting it thereto.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Experimental

General Information

All experiments were carried out under an atmosphere of argon. Flash column chromatography was performed over SiliCycle silica gel 230-400 mesh. $^1$H NMR, $^{19}$F NMR and $^{13}$C NMR spectra were acquired by Varian Mercury-400 MHz. The proton signal of residual non-deuterated solvent (δ 7.26 ppm for $CHCl_3$) was used as an internal reference for $^1$H spectra. NMR chemical shifts (δ) are reported in ppm and coupling constants (J) are reported in Hz. NMR split patterns are abbreviated as follows: s (singlet), d (doublet), t (triplet), dd (doublet of doublets) and m (multiplet). High resolution mass spectra were obtained using an Agilent 6210 ESI-TOF mass spectrometer.

Commercially obtained chemicals were used without further purification and all reactions were set up using anhydrous solvent from a dry solvent system (JC Meyer Solvent System) then degassed under argon. Copper powder was obtained for Sigma Aldrich: 99%, spherical and 10 μm in diameter. n-Butyl lithium solutions were diluted to the required concentration with HPLC grade hexanes. Quench columns were made using SiliCycle silica gel 230-400 mesh that was further dried by heating it to 135-140° C. under vacuum for 3-5 days. N-trifluoroacetylmorpholine was synthesized according to literature procedure and all corresponding characterization was comparable to the literature. Characterization of all compounds previously reported also corresponds to their literature i.e. WO2012097510, WO 9814436 A1 and A. Correia; D. T. McQuade; P. H. Seeberger, *Adv. Synth. Catal.* 2013, 355, 3517-3521.

Examples 1 to 6

General Procedure and Equipment Used for Trifluoroacylation in Flow

A Vapourtec E-Series System was utilized in for pumping of reagents with the compatible pump tube: i.e. n-butyl lithium in hexanes, 1,4-dichlorobenzene in THF, and N-trifluoroacetylmorpholine in THF. All solvents and reagent stock solutions were kept under an atmosphere of dry argon. The flow reactor was built using 1.6 mm (1/16") O.D.×0.3 mm (0.012") I.D. PTFE tubing and connected by ETFE T-mixers. Quench columns were made using FEP tubing (5/16") O.D.×(0.025") I.D., and connected in-line using 5/16 inch ETFE flangeless ferrules, 5/16 inch 1/2-20 Peek flangeless nuts and female 5/16-24 to male 1/14-28 KEL-F® (PCTFE) adapters. All tubing, connectors and adapters were purchased from IDEX Health and Science. Quench columns were prepared with the required amount of dry silica and the ends of the column were packed with short plugs of glass wool to prevent leaching of silica and clogging of the tubing.

A general setup was chosen as shown in FIG. 2.

Standard Flow Conditions:

Dichlorobenzene (PDCB) was dissolved in anhydrous, degassed THF (D1) to a concentration of 1.75 M. nBuLi (1.6 M in hexanes from Sigma Aldrich) was diluted to a concentration of 1.5 M in dry degassed hexanes and the limiting reagent, trifluoroacetyl morpholide (TFAM), was dissolved to a concentration of 1 M in dry degassed THF (D2). All reagent solutions were prepared and kept under argon. The E-Series and reactor loops were set up as described above. The temperature of the chiller 50, an ethanol cold bath was maintained at −45° C. using a HUBER TC50E chiller. The temperature in the chiller 51, also being an ethanol cold bath was maintained at −10° C. using liquid nitrogen and dry ice. The whole reactor was first flushed with anhydrous, degassed solvent, the reaction was performed on a 0.5 mmol scale with respect to trifluoroacetyl morpholide (4 minute pumping at a flow rate of 0.125 mL/min). To ensure complete quenching and capture of morpholine, a quench column of 2.0 or 2.5 grams of dry silica was used per 0.5 mmol reagent. Flow rates were adjusted to 0.125 ml/min via pumps 32, 34 and 38a. The volumes of the reaction zones were 1 ml for reaction zone 1 (36), 5 ml for reaction zone 2 (40) and 0.5 ml for the further reaction zone (42).

For optimization: Quench columns were made using 2.0 grams of dry silica (per 0.5 mmol of limiting reagent). The yellow solution containing the product 2 was collected and the solvent removed under vacuum. Mesitylene was then added as an internal standard for yield determination.

For determination of a two-step isolated yield: The scavenging column (43) was made using 2.5 grams of dry silica (per 0.5 mmol of limiting reagent). The crude yellow solution was collected at the end of the scavenging column (43) and kept refrigerated (−20° C.) until use for the second step.

Table 1 shows the results of the trifluoroacylation using varying reaction parameters

TABLE 1

| Example | Deviation from standard flow conditions | Yield (%)* |
|---|---|---|
| 1 | None | 87 |
| 2 | −55° C. | 61 |
| 3 | −35° C. | 70 |
| 4 | Reaction zone 2: Volume 3 mL (8 min residence time) | 78 |
| 5 | Reaction zone 2: Volume 7 mL (18.67 min residence time) | 74 |
| 6 | 1.2M concentration of TFAM | 73 |

*NMR yields based on mesitylene internal standard.

Examples 7 to 11

General Procedure and Equipment Used for Alkynylation in Flow

A Vapourtec E-Series System was utilized for pumping of reagents with the compatible pump tube: i.e. n-Butyl lithium in hexanes, cyclopropylacetylene in THF, and 1-(2,5-dichlorophenyl)-2,2,2-trifluoroethanone of formula (IV) (IP) obtained by example 1 in a mixture of hexanes and THF. All solvents and reagent stock solutions were kept under an atmosphere of dry argon. The flow reactor was built using 1.6 mm (1/16") O.D.×0.3 mm (0.012") I.D. PTFE tubing and connected by ETFE T-mixers. All tubing, connectors and adapters were purchased from IDEX Health and Science. All reagent solutions were prepared and kept under argon. The E-Series and reactor zones were set up as described in FIG. 3 and the corresponding description above. The temperature the chiller (70) was maintained at −20° C. using a HUBER TC50E chiller.

General Flow Conditions:

1-(2,5-dichlorophenyl)-2,2,2-trifluoroethanone of formula (IV) (IP) obtained by example 1 at a concentration of 0.33 M was used. nBuLi (1.6 M in hexanes from Sigma Aldrich) was diluted to a concentration of 0.43 M with anhydrous, degassed hexanes. Cyclopropylacetylene (C) was dissolved to a concentration of 0.5 M in anhydrous degassed THF (D3). The E-Series and reactor zones were set up as described above. The reaction was done on a 0.5 mmol scale of IP (1 minute pumping at a flow rate of 0.5 mL/min). The reactor was first flushed with anhydrous, degassed solvent.

The volumes of the reaction zones were 1 ml for reaction zone 3 (66) and 3 ml for reaction zone 4 (81).

For optimization: 1-(2,5-dichlorophenyl)-2,2,2-trifluoroethanone of formula (IV) (IP) obtained by example 1 (kept in the freezer at −20° C.) was re-dissolved in 2:1 THF: Hexanes mixture to a concentration of 0.33 M. The dark yellow solution containing product P—OH was quenched in cold brine (ice bath) and extracted with ethyl acetate (3×20 mL). The solvent was removed under vacuum, NMR conversions were determined based on fluorine NMR.

For determination of a two-step isolated yield: 1-(2,5-dichlorophenyl)-2,2,2-trifluoroethanone of formula (IV) (IP) obtained by example 1 was used directly after collection from example 1. The reaction was performed assuming full conversion on a 0.5 mmol scale of limiting reagent (TFAM). The dark yellow solution was quenched in cold brine (ice bath) and extracted with ethyl acetate (3×20 mL). The solvent was then removed under vacuum. Product alcohol 2 was isolated from the brown oil by flash column chromatography using 10:1 Hexanes:EtOAc as a pale yellow oil. (112.4 mg-73% yield over steps A) to D)).

Table 2 shows the results of the alkynylation using varying reaction parameters

TABLE 2

| Example | Rate (mL/min) | T (° C.) | Residence Time Reaction zone 3 (s)/ Reaction zone 4 (s) | Conversion (%) |
|---|---|---|---|---|
| 7 | 1.0 | −20 | 30 /60 | 90 |
| 8 | 0.5 | −20 | 60 /120 | 93 |
| 9 | 0.25 | −20 | 120 /240 | 92 |
| 10 | 0.5 | −5 | 60 /120 | 67 |
| 11 | 0.5 | −20 | 60 /120 | 92 (73)* |

*isolated yield over steps A) to D)

Examples 12 to 21

General Procedure for Copper Catalyzed Cyclization in Batch

Pure 4-cyclopropyl-2-(2,5-dichloro-phenyl)-1,1,1-trifluoro-but-3-yn-2-ol (0.1 mmol, 31 mg), NaOCN (0.2 mmol, 13 mg) and CuI (0.02 mmol, 3.8 mg) were placed in a 2-5 mL sealable borosilicate tube with magnetic stir bar and aluminium crimp cap. The tube was evacuated and backfilled with argon, then 0.5 mL anhydrous, degassed toluene was added and the tube was flushed again with argon. Trans-N,N'-dimethyl-1,2-cyclohexanediamine (0.08 mmol, 13 μL) was then added, followed by another 0.5 mL toluene. The tube was flushed with argon again, sealed, and placed in an oil bath at 120° C. for 16 hours. The heterogeneous mixture was allowed to cool and was then filtered with ethyl acetate (3-5 mL) through a short column of silica gel and concentrated under vacuum. NMR yields were obtained using mesitylene as an internal standard.

Table 3 shows the results of the copper catalysed cyclization in batch

TABLE 3

| Example | [Cu] (mol %) | Ligand (Cu:L ratio) | Yield (%) |
|---|---|---|---|
| 12* | CuI (20) | DMEDA(1:2) | Trace |
| 13* | CuI (20) | Phen (1:2) | 0 |
| 14* | CuI (20) | CyDMEDA (1:2) | 12 |
| 15 | CuI (20) | CyDMEDA (1:4) | 42 |
| 16** | CuI (20) | CyDMEDA (1:4) | n.d |
| 17 | (CuOTf)$_2$•benzene | CyDMEDA (1:4) | 36 |
| 18 | Cu(MeCN)$_4$BF$_4$ | CyDMEDA (1:4) | 48 |
| 19 | CuSO$_4$ (20) | CyDMEDA (1:4) | 62 |

TABLE 3-continued

| Example | [Cu] (mol %) | Ligand (Cu:L ratio) | Yield (%) |
|---|---|---|---|
| 20 | Cu(NO$_3$)$_2$·3H$_2$O | CyDMEDA (1:4) | 60 |
| 21*** | CuI (20) | CyDMEDA (1:4) | 9 |

*Performed in 1 mL dioxane
**10 mol % tetrabutylammonium chloride added.
***Performed under air.
CyDMEDA: (trans-N,N'-dimethyl-1,2-cyclohexane-diamine),
DMEDA: (N,N'-dimethyl-1,2-ethylene diamine),
Phen: (phenanthroline),
n.d.: none detected.

Examples 22 to 27

General Procedure for Copper Catalyzed Cyclization in Flow
Standard Procedure for Flow Optimization:

Design for packed bed: A reactor according to FIG. 1 was used. The reaction zone (16) was built using OMNIFIT HiT glass columns (6.6 mm internal diameter, 100 mm height, 40 μm PTFE frit filters, adjustable end caps). NaOCN (20 equiv., 130 mg) and Celite (750 mg) was thoroughly mixed and packed tightly into the reaction zone. After packing the reaction zone had an internal volume of approximately 2.0 mL. The reactor was assembled as shown in FIG. 1 using the Vapourtec E-series fitted with a standard column heated reactor and a manual injection loop as feeding zone (11). The injection loop (2 mL) was built using (1.6 mm O.D.×0.3 mm I.D.) PTFE tubing connected to the main stream using two switchable 3-way (HEX) valves obtained from OMNIFIT.

Injection loop: Pure 4-cyclopropyl-2-(2,5-dichloro-phenyl)-1,1,1-trifluoro-but-3-yn-2-ol (0.1 mmol, 31 mg, IP), and copper nitrate tri-hydrate (0.02 mmol, 3.8 mgs) were placed in a pear shaped flask and the flask was evacuated and backfilled three times with argon. Anhydrous, degassed acetonitrile (1 mL) was added and the flask was flushed again with argon. Trans-N,N'-dimethyl-1,2-cyclohexanediamine (0.08 mmol, 12.6 μL) was injected, followed by 1 mL anhydrous, degassed toluene. The solution was sonicated to ensure homogeneity and transferred to the manual injection loop under argon.

Flow conditions: The reactor was first flushed with anhydrous toluene and then heated under 0.7 MPa until the column temperature was recorded at 120° C. for a flow rate of 33 μl/min (corresponding to a residence time of 60 minutes). The manual valves were then switched to allow injection of the reagent stream into the column reactor. The resulting mixture was collected and filtered with ethyl acetate (approx. 10 mL) through a short column of silica gel and concentrated under vacuum. Conversions of the crude mixture were determined based on fluorine NMR.

Table 4 shows the results of the copper catalysed cyclization in flow-through reactor

TABLE 4

| Example | [Cu] (mol %) | Cu]/L (mol %) | Cu° (equiv) | Conc. IP [M] | Conversion** of IP (%) | to P—OH (%) |
|---|---|---|---|---|---|---|
| 22 | Cu(NO$_3$)$_2$ × 3H$_2$O | 5/10 | 1 | 0.05 | 90 | 44 |
| 23 | Cu(NO$_3$)$_2$ × 3H$_2$O | 5/20 | 1 | 0.05 | 93 | 41 |
| 24 | Cu(NO$_3$)$_2$ × 3H$_2$O | 5/20 | 2 | 0.05 | 97 | 35 |
| 25* | — | 0/10 | 1 | 0.05 | 100 | n.d |
| 26 | Cu(OTf)$_2$ | 5/10 | 0.5 | 0.15 | 91 | 63 |

*for comparison only, not according to the invention
**Conversions based on $^{19}$F NMR.

Example 27

Pure 4-cyclopropyl-2-(2,5-dichloro-phenyl)-1,1,1-trifluoro-but-3-yn-2-ol (0.4 mmol, 124 mg), and copper (II) triflate (0.02 mmol, 7.2 mg) were placed in a pear shaped flask and the flask was evacuated and backfilled three times with argon. Anhydrous, degassed acetonitrile (0.5 mL) was added and the tube was flushed again with argon. Trans-N,N'-dimethyl-1,2-cyclohexanediamine (0.04 mmol, 6.3 μL) was injected, followed by 1.5 mL anhydrous, degassed toluene. The solution was sonicated to ensure homogeneity and transferred to the manual injection loop under argon. The packed bed column was built using OMNIFIT HiT glass columns (6.6 mm internal diameter, 100 mm height, 40 μm PTFE frit filters, adjustable end caps). NaOCN (20 equiv., 520 mg), Celite (700 mg), and copper powder (0.2 mmol, 13 mg) were thoroughly mixed and packed into the column. After packing the column had an internal volume of approximately 2.0 mL. The reaction was performed at a flow rate of 33 μl/min; corresponding to a residence time of 60 mins. The collected crude mixture was diluted with ethyl acetate (approx. 10 mL) and filtered through a short column of silica, followed by a plug of neutral alumina to remove the copper salts. Solvent was removed under vacuum to obtain a pale yellow solid. The purified compound, rac-Efavirenz, was obtained as an off-white solid by crystallization with hexanes:dichloromethane 78.0 mg, 62% yield).

Main other product in examples 12 to 27 was 2-(3-chlorophenyl)-4-cyclopropyl-1,1,1-trifluorobut-3-yn-2-ol.

NMR Data:

2-(3-chlorophenyl)-4-cyclopropyl-1,1,1-trifluorobut-3-yn-2-ol $^1$H NMR (400 MHz, CDCl$_3$, ppm) δ 7.71 (s, 1H), 7.60 (d, J=7.6 Hz, 1H), 7.39-7.31 (m, 2H), 3.03 (s, 1H), 1H), 1.40-1.34 (m, 1H); 0.92-0.79 (m, 4H);
$^{13}$C NMR (100 MHz, CDCl$_3$, ppm) δ 137.6, 134.1, 129.5, 129.3, 127.5, 125.4, 123.1 (q, J$_{C-F}$=284 Hz), 93.1, 72.3 (q, J$_{C-F}$=32 Hz), 70.5, 8.5, 0.7;
$^{19}$F NMR (376 MHz, CDCl$_3$, ppm) δ −80.57.
HRMS (ESI) m/z (M-H)$^+$ calculated: 273.0300, found: 273.0325.
LRMS (ES) m/z (M)$^+$ calculated: 274.0372, found: 274.0361.

The invention claimed is:

1. A process for the preparation of 6-chloro-4-(2-cyclopropylethynyl)-4-(trifluoromethyl)-1H-3,1-benzoxazin-2-one comprising reacting 4-cyclopropyl-2-(2,5-dichloro-phenyl)-1,1,1-trifluoro-but-3-yn-2-ol with at least one cyanate in the presence of at least one transition metal compound;
wherein the at least one cyanate is selected from the group consisting of alkali cyanates and alkaline earth cyanates; and
wherein the at least one transition metal compound is selected from the group consisting of copper, nickel, palladium, rhodium and platinum compounds.

2. The process according to claim 1, wherein the at least one cyanate comprises sodium cyanate.

3. The process according to claim 1, wherein the at least one transition metal compound is selected from formulae (Ia), (Ib), (IIa), (IIb) and (III), $$M(Y^1)_2 \qquad (Ia)$$

and $$M(Y^2) \qquad (Ib),$$

wherein
M is independently nickel, palladium or copper(II) for formula (Ia) and formula (Ib);
$Y^1$ is chloride, bromide, acetate, nitrate, methanesulphonate, trifluoromethane-sulphonate, trifluoroacetate or acetylacetonate; and
$Y^2$ is sulphate;

$$MY^3 \qquad (IIa)$$

and $$[M(B)_4](Y^3) \qquad (IIb),$$

wherein
M is copper(I) for formula (IIa) and formula (IIb);
$Y^3$ is chloride, bromide, iodide, acetate, methanesulphonate, trifluoromethanesulphonate, tetrafluoroborate, trifluoroacetate, hexafluorophosphate, perchlorate, hexafluoroantimonate, tetra(3,5-bistrifluoromethylphenyl)borate or tetraphenylborate; and
B is a nitrile; and $$[M(D)_2] \qquad (III),$$

wherein
M is palladium or nickel for formula (III); and
D is a $(C_4-C_{12})$-diene.

4. The process according to claim 1, wherein the at least one transition metal compound is selected from the group of copper(I) iodide, copper(II) triflate, copper(II) nitrate trihydrate, copper sulphate, and copper(I) tetraacetonitrile tetrafluoroborate.

5. The process according to claim 1, wherein the at least one transition metal compound is used in combination with at least one ligand capable of coordinating to the transition metal of the at least one transition metal compound, wherein the transition metal is copper, nickel or palladium.

6. The process according to claim 5, wherein the at least one ligand is selected from the group consisting of diamines, carbenes, phosphines, phosphites phenanthrolines, hydroxyquinolines, bis imines, bipyridines, salicylamides, pyrrolidines, glycine, proline, sparteine, and mixtures thereof.

7. The process according to claim 5, wherein the at least one ligand is selected from the group consisting of phenanthroline, N,N'-dimethyl-1,2-diaminoethan (DMEDA) and N,N'-dimethyl-1,2-diaminocyclohexane (CyDMEDA).

8. The process according to claim 5, wherein the at least one ligand is employed in an amount of from 0.5 to 10 mol per mol of the transition metal compound employed and calculated on the transition metal content present in the transition metal compound.

9. The process according to claim 1, wherein the process is carried out in absence of phase transfer catalysts.

10. The process according to claim 1, wherein copper (II) compounds are employed and additionally copper(0).

11. The process according to claim 3, wherein copper (II) compounds are employed and additionally copper(0).

12. The process according to claim 1, wherein the process is carried out batchwise or continuously.

13. The process according to claim 1, wherein (4S)-4-cyclopropyl-2-(2,5-dichloro-phenyl)-1,1,1-trifluoro-but-3-yn-2-ol is employed with an enantiomeric excess (ee) of at least 80%.

14. The process of claim 10, wherein the copper(0) is in form of finely divided elemental copper.

15. The process of claim 11, wherein the copper(0) is in form of finely divided elemental copper.

16. The process of claim 13, wherein (4S)-4-cyclopropyl-2-(2,5-dichloro-phenyl)-1,1,1-trifluoro-but-3-yn-2-ol is employed with an enantiomeric excess (ee) of at least 90%.

17. The process of claim 13, wherein (4S)-4-cyclopropyl-2-(2,5-dichloro-phenyl)-1,1,1-trifluoro-but-3-yn-2-ol is employed with an enantiomeric excess (ee) of at least 95%.

18. The process of claim 3, wherein the nitrile is acetonitrile, benzonitrile or benzyl nitrile.

19. The process of claim 3, wherein the $(C_4-C_{12})$-diene is norbornadiene or 1,5-cyclooctadiene.

* * * * *